(12) United States Patent
Park et al.

(10) Patent No.: US 8,337,406 B2
(45) Date of Patent: Dec. 25, 2012

(54) ADAPTIVE PERSISTENCE PROCESSING OF ELASTIC IMAGES

(75) Inventors: Sang Shik Park, Seoul (KR); Mok Kun Jeong, Seoul (KR); Chul An Kim, Seoul (KR); Jong Sik Kim, Seoul (KR)

(73) Assignee: Medison Co., Ltd., Kangwon-do (KR)

( * ) Notice: Subject to any disclaimer, the term of this patent is extended or adjusted under 35 U.S.C. 154(b) by 263 days.

(21) Appl. No.: 12/623,250

(22) Filed: Nov. 20, 2009

(65) Prior Publication Data

US 2010/0125205 A1     May 20, 2010

(30) Foreign Application Priority Data

Nov. 20, 2008   (KR) ........................ 10-2008-0115641

(51) Int. Cl.
*A61B 8/00*          (2006.01)

(52) U.S. Cl. ........ 600/437; 600/438; 600/443; 600/440; 600/441

(58) Field of Classification Search .................. 600/437, 600/438, 443, 440, 441
See application file for complete search history.

(56) References Cited

U.S. PATENT DOCUMENTS

| 6,558,324 B1 | 5/2003 | Von Behren et al. |
| 2004/0015079 A1 | 1/2004 | Berger et al. |
| 2007/0197915 A1* | 8/2007 | Jeong et al. .................. 600/459 |
| 2008/0064956 A1* | 3/2008 | Jeong et al. .................. 600/438 |
| 2009/0292205 A1* | 11/2009 | Osaka .......................... 600/443 |

FOREIGN PATENT DOCUMENTS

| EP | 1900328 A1 | 3/2008 |
| JP | 2008-073417 | 4/2008 |
| KR | 10-2008-0024327 | 3/2008 |
| WO | WO 2008010500 A1 * | 1/2008 |
| WO | WO2008/132504 A1 | 11/2008 |

OTHER PUBLICATIONS

European Search Report for Application No. 09175352, mailed Dec. 17, 2009, 7 pages.
Pesavento et al., *System for real-time elastography*, Electronics Letters, vol. 35(11), 941-42 (1999).
Korean Office Action issued in Korean Patent Application No. 10-2008-0115641 dated Mar. 16, 2012.

* cited by examiner

*Primary Examiner* — Brian Casler
*Assistant Examiner* — Rajeev Siripurapu
(74) *Attorney, Agent, or Firm* — McDermott Will & Emery LLP

(57) ABSTRACT

Adaptive persistence processing on elastic images in an ultrasound system is disclosed. An ultrasound data acquisition unit sequentially acquires a plurality of ultrasound data frames based on ultrasound echo signals reflected from a target object by repeatedly applying and releasing stress to/from the target object. A processing unit calculates inter-frame displacements of the frames between the ultrasound data frames to form elastic images. The processing unit adaptively performs persistence processing on the elastic images in consideration of application or release of the stress to/from the target object.

6 Claims, 3 Drawing Sheets

ADAPTIVE PERSISTENCE PROCESSING OF ELASTIC IMAGES

The present application claims priority from Korean Patent Application No. 10-2008-0115641 filed on Nov. 20, 2008, the entire subject matter of which is incorporated herein by reference.

TECHNICAL FIELD

The present disclosure generally relates to ultrasound systems, and more particularly to an ultrasound system for adaptively performing persistence processing on elastic images.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional diagnostic images of internal features of an object (e.g., human organs).

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image.

To resolve the problem relating to recognizing the tumor, cancer and the like in the B-mode, an ultrasound elastic imaging technology has been developed to visualize mechanical characteristics of the tissues such as the elasticity thereof in the ultrasound system. Such technology is very helpful for diagnosing lesions such as tumor and cancer, which are hardly recognized in the B-mode image. The ultrasound elastic imaging technology may utilize the scientific property that the elasticity of the tissues is related to a pathological phenomenon. For example, the tumor or cancer is relatively stiffer than the neighboring normal tissues. Thus, when stress is uniformly applied, a displacement of the tumor or cancer is typically smaller than those of the neighboring tissues.

The elastic images may be acquired by using a stress applying unit, such as an ultrasound probe, to apply stress to the target object ("first time duration") and/or release the stress applied to the target object ("second time duration"). If the stress is applied to the target object by using the ultrasound probe, then lateral components in echo signals may be increased due to the motion of the ultrasound probe. Thus, the quality of the elastic image acquired by applying the stress may be lowered than that of the elastic image acquired by releasing the stress. Accordingly, there is a need to adaptively perform persistence processing on the elastic images according to the first and second time durations.

SUMMARY

An embodiment for adaptively performing persistence on elastic images is disclosed herein. In one embodiment, by way of non-limiting example, an ultrasound system comprises: a stress applying unit configured to apply a stress to a target object; an ultrasound data acquisition unit configured to transmit/receive ultrasound signals to/from the target object and sequentially acquire a plurality of ultrasound data frames indicative of the target object based on the received ultrasound signals, wherein the plurality of ultrasound data frames include at least two first ultrasound data frames acquired at a first time duration in which stress is applied to the target object and at least two second ultrasound data frames acquired at a second time duration in which the stress is released from the target object; and a processing unit configured to calculate first inter-frame displacements between the at least two first ultrasound data frames and second inter-frame displacements between the at least two second ultrasound data frames to form elastic images and adaptively perform persistence processing on the elastic images based on the first and second time inter-frame displacements.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
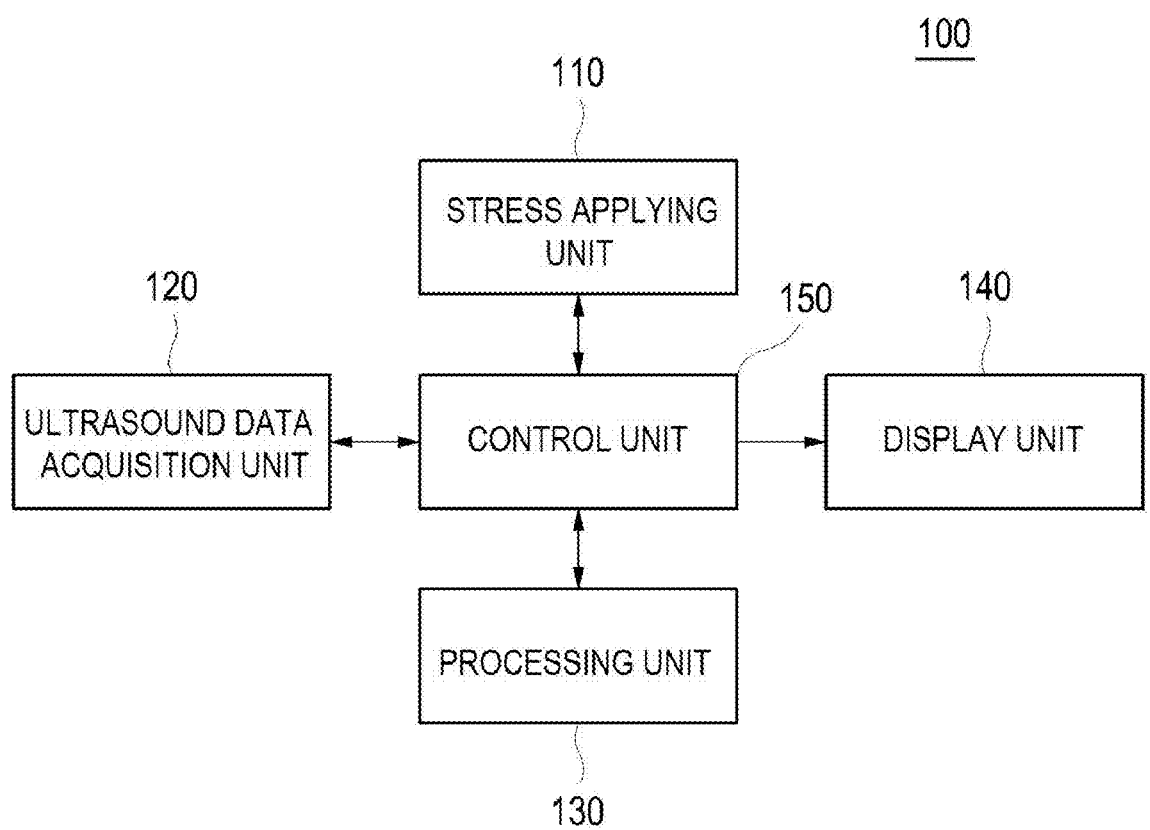
FIG. 1 is a block diagram showing an illustrative embodiment of an ultrasound system.

FIG. 1 is a block diagram showing an illustrative embodiment of an ultrasound system. Referring to FIG. 1, the ultrasound system 100 may include a stress applying unit 110 to apply stress to a target object. The ultrasound system 100 may further include an ultrasound data acquisition unit 120. The ultrasound data acquisition unit 120 may be operable to transmit/receive ultrasound signals to/from the target object to thereby form ultrasound data.

Figure 2:
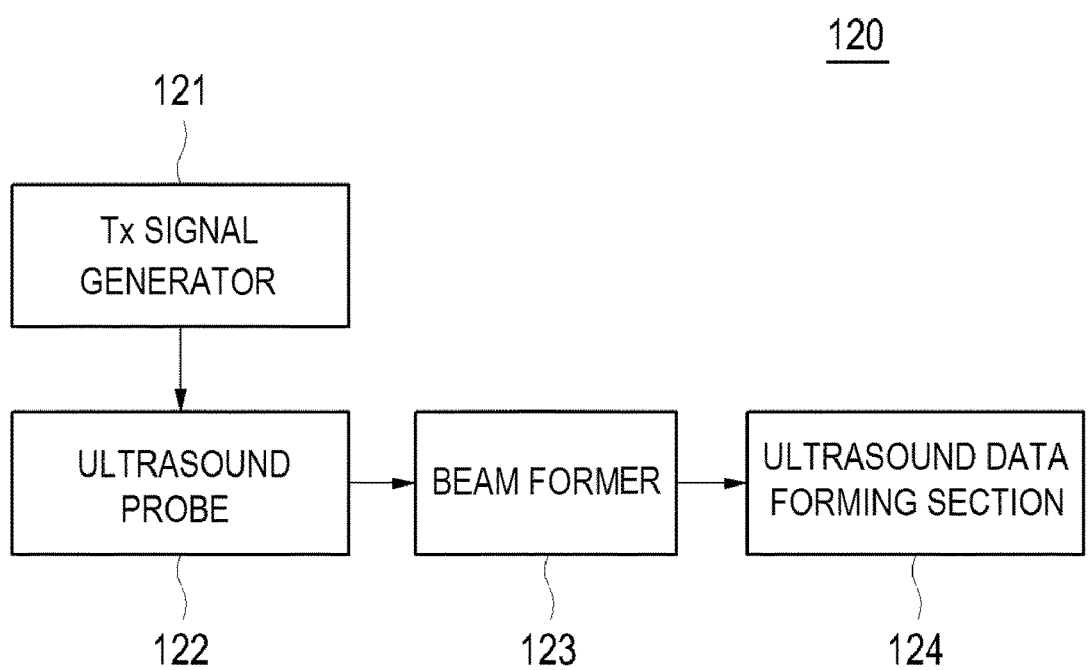
FIG. 2 is a block diagram showing an illustrative embodiment of an ultrasound data acquisition unit.

Referring to FIG. 2, the ultrasound data acquisition unit 120 may include a transmit (Tx) signal generator 121 that generates a plurality of Tx signals. The ultrasound data acquisition unit 120 may further include an ultrasound probe 122 coupled to the Tx signal generator 121. The ultrasound probe 122 may be operable to transmit the ultrasound signals to the target object in response to the Tx signals. The ultrasound probe 122 may be further operable to receive echo signals reflected from the target object to thereby form electrical receive signals. The ultrasound probe 122 may contain an array transducer consisting of a plurality of transducer elements. In one embodiment, the ultrasound probe 122 may include a convex probe, a linear probe, etc., although it is not limited thereto.

The ultrasound data acquisition unit 120 may further include a beam former 123. The beam former 123 may be operable to apply delays to the electrical receive signals in consideration of positions of the transducer elements and focal points. The beam former 123 may further sum the delayed receive signals to thereby output a plurality of receive-focused beams. The ultrasound data acquisition unit 120 may further include an ultrasound data forming section 124 that may be operable to form a plurality of ultrasound data frames based on the receive-focused beams. In one embodiment, by way of non-limiting example, the ultrasound data frames may be brightness-mode image data frames. The ultrasound data frames may be radio frequency data or in-phase/quadrature data frames, which are obtained while the stress is applied to the target object (hereinafter, referred to as "first time duration") and while the stress is released from the target object (hereinafter, referred to as "second time duration"). In one embodiment, a sensor (not shown) may be installed on a face of the stress applying unit 110 to measure the stress, which is applied to the target object, and determine the first time duration and the second time duration.

Referring back to FIG. 1, the ultrasound system 100 may further include a processing unit 130. The processing unit 130 may be operable to calculate displacements between neighboring ultrasound data frames, which are sequentially provided from the ultrasound data acquisition unit 120. The processing unit 130 may be further operable to form elastic images based on the calculated displacements. In one embodiment, the elastic images may include first elastic images corresponding to the first time duration and second elastic images corresponding to the second time duration. The processing unit 130 may be operable to perform persistence processing on the first elastic images and the second elastic images with different predetermined weights.

Figure 3:
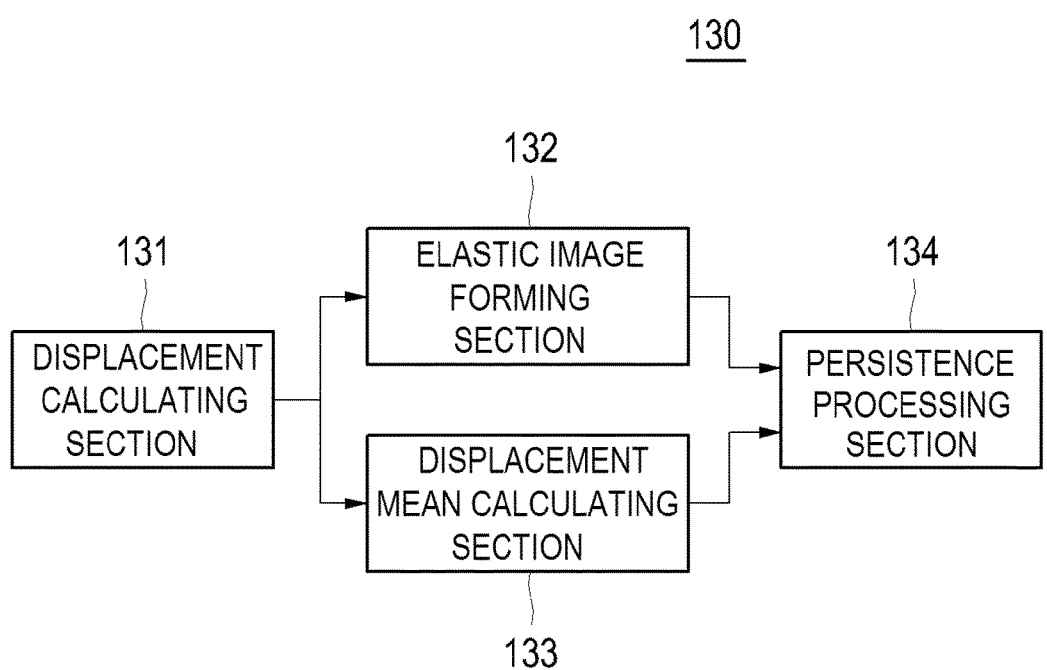
FIG. 3 is a block diagram showing an illustrative embodiment of a processing unit.

FIG. 3 is a block diagram showing an illustrative embodiment of the processing unit 130. Referring to FIG. 3, the processing unit 130 may include a displacement calculating section 131. The displacement calculating section 131 may be operable to calculate inter-frame displacements between the neighboring ultrasound data frames. In one embodiment, by way of non-limiting example, the displacement calculation may be performed by using inter-frame cross-correlation upon the ultrasound data frames on a pixel or block (e.g., 4×4 pixels, 8×8 pixels, etc.) unit basis. The displacements may include first displacements calculated from the ultrasound data frames, which are obtained at the first time duration, and second displacements calculated from the ultrasound data corresponding to frames, which are obtained at the second time duration. The first and second displacements may have different signs. For example, the first displacements may have a positive sign, while the second displacements may have a negative sign.

The processing unit 130 may further include an elastic image forming section 132. The elastic image forming section 132 may be operable to sequentially form elastic images based on the calculated displacements.

The processing unit 130 may further include a displacement mean calculating section 133. The displacement mean calculating section 133 may be operable to calculate a displacement mean of the displacements associated with each of the elastic images. In one embodiment, by way of non-limiting example, the displacement mean calculated from the first displacements may be set to have a positive sign, while the displacement calculated from the second displacements may be set to have a negative sign.

The processing unit 130 may further include a persistence processing section 134 coupled to the elastic image section 132 and the displacement mean calculating section 133 to thereby receive the elastic images and the displacement means corresponding to the respective elastic images. The persistence processing section 134 may be operable to set first and second predetermined weights based on the displacement means. The first predetermined weight is applied to a current elastic image, while the second predetermined weight is applied to a previous elastic image persistence-processed. In one embodiment, the first and second predetermined weights may be set such that the sum thereof is "1." For example, if the displacement mean having a positive sign corresponding to the current elastic image is provided, then the persistence processing section 134 may set the first predetermined weight less than the second predetermined weight. For example, the first predetermined weight may be set to 0.2 and the second predetermined weight may be set to 0.8. On the other hand, if the displacement mean having a negative sign is provided corresponding to the current elastic image, then the persistence processing section 134 may set the first predetermined weight to 0.8 and the second predetermined weight to 0.2.

The persistence processing section 134 may apply the first predetermined weight to the current elastic image and the second predetermined weight to the previous elastic image. The persistent processing section 134 may further compound the weighted current elastic image and the weighted previous elastic image to thereby output a compound image as an elastic image persistence-processed. The persistence processing section 134 may be operable to perform persistence processing as follows.

$$S_{out(N)} = P \times S_{in(N)} + (1-P) \times S_{out(N-1)} \qquad (1)$$

wherein $S_{out(N)}$ represents the elastic image persistence-processed, $S_{in(N)}$ represents the current elastic image, $S_{out(N-1)}$ represents the previous elastic image, P represents the first predetermined weight and (1−P) represents the second predetermined weight. Accordingly, if P is 0, $S_{in(N)}$ is removed and $S_{out(N-1)}$ is only outputted. On the other hand, if P is 1, $S_{in(N)}$ is only outputted without the persistence processing.

The persistence processing section 134 may be further operable to calculate a sign change rate from the displacement means. That is, the persistence processing section 134 may be operable to calculate the sign change rate of the displacement means from positive to negative, and vice versa. The persistence processing section 134 may be operable to compare the calculated sign change rate with a first predetermined threshold. If the sign change rate is greater than the first predetermined threshold, then the persistence processing section 134 may be operable to apply a third predetermined weight to the current elastic image. In one embodiment, the third predetermined weight may be set within a range from 0 to the first predetermined weight.

Further, the persistent processing section 134 may be operable to calculate a magnitude of the second displacement mean. The persistent processing section 134 may compare the calculated magnitude of the second displacement mean with a second predetermined threshold. If the magnitude of the second displacement mean is greater than the second predetermined threshold, then the persistent processing section 134 may apply a fourth predetermined weight to the current elastic image. In one embodiment, the fourth predetermined weight may be set within a range of from first predetermined weight to the second predetermined weight.

Referring back to FIG. 1, the elastic image persistence-processed is displayed on the display unit 140. The ultrasound system 100 may further include a control unit 150. The control unit 150 may be operable to control the transmission and reception of the ultrasound signals in the ultrasound data acquisition unit 120. Further, the control unit 150 may be further operable to control the operations of the processing unit 130.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
a stress applying unit configured to apply stress to a target object;
an ultrasound data acquisition unit configured to transmit/receive ultrasound signals to/from the target object and sequentially acquire a plurality of ultrasound data frames indicative of the target object based on the received ultrasound signals, wherein the plurality of ultrasound data frames include at least two first ultrasound data frames acquired at a first time duration in which stress is applied to the target object and at least two second ultrasound data frames acquired at a second time duration in which the stress is released from the target object; and
a processing unit configured to calculate first inter-frame displacements between the at least two first ultrasound data frames and second inter-frame displacements between the at least two second ultrasound data frames to form elastic images and apply a different predetermined weight to each of the elastic images for persistence processing according to whether the calculated inter-frame displacements are the first inter-frame displacements or the second inter-frame displacements,
wherein the processing unit includes:
an elastic image forming section configured to sequentially form a plurality of elastic images based on the first and second inter-frame displacements;
a displacement mean calculating section configured to calculate a displacement mean of each of the first and second inter-frame displacements corresponding to each of the elastic images, wherein the displacement mean calculating section is further configured to set displacement means calculated from the first inter-frame displacements and displacement means calculated from the second inter-frame displacements, and wherein the displacement means calculated from the first inter-frame displacements and the displacement means calculated from the second inter-frame displacements have different signs; and
a persistence processing section configured to set first and second predetermined weights based on a sign of the displacement mean corresponding to the current elastic image, and perform the persistence processing on the elastic images by applying the first predetermined weight to the current elastic image and the second predetermined weight to a previous elastic image persistence-processed.

2. The ultrasound system of claim 1, wherein the stress applying unit includes a sensor installed on a face thereof to measure the stress applied to the target object and determine the first time duration and the second time duration.

3. The ultrasound system of claim 1, further comprising a display unit to display the elastic images.

4. The ultrasound system of claim 1, wherein the persistence processing section is configured to:
calculate a sign change rate of the displacement means from positive to negative, and vice versa;
compare the sign change rate with a first predetermined threshold; and
if the sign change rate is greater than the first predetermined threshold, apply a third predetermined weight to the current elastic image, wherein the third predetermined weight is set within a range of from 0 to first determined weight.

5. The ultrasound system of claim 1, wherein the persistence processing section is configured to:
calculate magnitude of the second displacement mean;
compare the calculated magnitude with a second predetermined threshold; and
if the calculated magnitude is greater than the second predetermined threshold, apply a fourth predetermined weight to the current elastic image, wherein the fourth predetermined weight is set within a range of from the first weight to the second weight.

6. The ultrasound system of claim 1, wherein the stress applying unit is configured to set the first time duration to be shorter than the second time duration.

* * * * *